United States Patent [19]

Robinson et al.

[11] Patent Number: 5,137,828
[45] Date of Patent: Aug. 11, 1992

[54] BIOMASS PRODUCTION APPARATUS

[75] Inventors: Lee F. Robinson, London; Angus W. Morrison, South Godstone, both of England

[73] Assignee: Biotechna Limited, London, England

[21] Appl. No.: 684,500

[22] Filed: Apr. 15, 1991

Related U.S. Application Data

[63] Continuation of Ser. No. 23,393, Mar. 9, 1987, abandoned.

[30] Foreign Application Priority Data

Mar. 19, 1986 [GB] United Kingdom ............... 8606817
Jun. 11, 1986 [GB] United Kingdom ............... 8614249
Sep. 23, 1986 [GB] United Kingdom ............... 8622818

[51] Int. Cl.$^5$ .............................................. C12M 1/24
[52] U.S. Cl. ................................. 435/296; 435/287; 435/293; 435/311; 435/313; 435/316
[58] Field of Search ............ 435/287, 293, 311, 313, 435/316, 296; 422/22, 24; 210/603, 605, 602, 610, 630; 126/442, 443

[56] References Cited

U.S. PATENT DOCUMENTS

| | | | |
|---|---|---|---|
| 2,658,310 | 11/1953 | Cook | 47/1.4 X |
| 2,715,795 | 8/1955 | Pallotta et al. | 47/1.4 X |
| 3,218,758 | 11/1965 | Konikoff | 435/313 X |
| 3,303,608 | 2/1967 | Hannan | 435/313 X |
| 3,814,680 | 6/1974 | Wood | 422/24 X |
| 3,959,923 | 6/1976 | Selke | 435/287 X |
| 4,267,826 | 5/1981 | Hitt, Jr. | 126/443 X |
| 4,473,970 | 10/1984 | Hills | 47/1.4 |
| 4,676,896 | 6/1987 | Norton | 422/24 X |
| 4,724,214 | 2/1988 | Mori | 435/313 X |
| 4,769,131 | 9/1988 | Noll et al. | 422/24 X |

FOREIGN PATENT DOCUMENTS

| | | |
|---|---|---|
| 1299164 | 7/1969 | Fed. Rep. of Germany . |
| 909092 | 9/1944 | France ........................ 126/442 |
| WO86/05201 | 9/1986 | PCT Int'l Appl. . |
| 1062258 | 12/1983 | U.S.S.R. . |
| 2118572 | 11/1983 | United Kingdom . |

Primary Examiner—Robert J. Warden
Assistant Examiner—Amalia Santiago
Attorney, Agent, or Firm—Armstrong, Nikaido, Marmelstein, Kubovcik & Murray

[57] ABSTRACT

The production of biomass, such as algae, is carried out in a substantially transparent tube wound on an upstanding core structure. The exterior surface of the tube is exposed to natural light and the tube and/or the core is adapted to encourage light penetration into the tube in the region of contact between the tube and the core structure.

8 Claims, 4 Drawing Sheets

BIOMASS PRODUCTION APPARATUS

This application is a continuation of application Ser. No. 023,393 filed Mar. 9, 1987, now abandoned.

FIELD OF THE INVENTION

This invention relates to biomass production and is particularly concerned with a photobioreactor and a method of biomass production employing such a photobioreactor.

BACKGROUND OF THE INVENTION

The long term commercial potential of producing useful products by photosynthesis techniques using simple plant matter, such as algae and seaweed, has been recognised for some time. Indeed the ability of simple single cell organisms, such as blue green algae, to utilise sunlight, carbon dioxide and the inorganic constituents of sea water to produce more complex matter played an essential part in the evolutionary process. Many attempts have been made to harness the ability of simple organisms to produce complex materials.

Open channel cultivation of algae has been attempted to produce a biomass for animal or human consumption. Not surprisingly this comparatively crude method has proved impracticable for production of pure high grade products because of such problems as invasion by hostile species (sometimes producing dangerous toxins), other pollution (such as dust), difficulty in the control of such variables as nutrient ratios, temperature and pH, intrinsically low yield because of escape of carbon dioxide to the atmosphere and inefficient use of light to illuminate only the top portion of the biomass.

Somewhat more sophisticated attempts have involved the use of horizontally disposed large diameter transparent plastics tubes for biomass production, e.g. Italian Patent Application No. 21522 A/78. The problems of such a system include the low density of biomass in the liquid within the tubes, coating of the pipes by algae due to low velocity flow therethrough thus reducing transparency, overheating in summer weather and high land usage.

As an alternative, a construction has been proposed in U.K. Patent No. 2118572 comprising flat vertical panels, (of area about 1 square meter) having a pipe of comparatively small diameter wound substantially horizontally against the panel face thereof. Again the land usage is high, in that each square meter of plant requires a square meter of ground area for its installation. Furthermore, the process control problems of manipulating a sufficiently large number of such units for commercial production are enormous. The design of the panels gives an inherently unstable construction unable to withstand adverse weather conditions.

Other problems encountered include the growth of unwanted microscopic species, such as bacteria, amoeba and rotifers within the biomass culture, particularly when operating in open cultures.

OBJECTS OF THE INVENTION

It is an object of this invention to provide an improved biomass production process which can be carried out on a substantial commercial scale with reduced land usage and improved operating efficiency. It is a further object of this invention to provide an improved photobioreactor for use on a substantial commercial scale with reduced land usage and improved operating efficiency.

SUMMARY OF THE INVENTION

According to this invention we provide a method of biomass production comprising causing a synthesis mixture comprising living plant matter, such as algae, bacteriophages and seaweeds, together with essential nutrients for growth of the plant matter, to flow through a substantially transparent tube wound on an upstanding core structure, the exterior of the wound tube being exposed to natural light, and the tube and/or the core being provided with means to encourage light penetration into the tube in the region of contact between the tube and the core structure, subjecting the flowing synthesis mixture to light energy and withdrawing a biomass synthesis product stream from the mixture.

According to a further aspect of the invention we provide a photobioreactor comprising an upstanding core structure, a substantially transparent tube wound on the core structure so that, in use the exterior of the wound tube is exposed to natural light, means to encourage light penetration into the tube in the region of contact between the tube and the core structure, means for causing a synthesis mixture to flow through the wound tube and means for withdrawing a biomass synthesis product stream.

DESCRIPTION OF THE PREFERRED EMBODIMENTS

The means to encourage light penetration may comprise providing the tube and/or the core with light reflecting means adjacent the area of contact between the tube and the core structure. The light reflecting means are suitably provided by interposition of a material such as aluminium foil between the core structure and wound tube. As an alternative, the core structure may be painted white and/or provided with a reflective surface, for example of small glass balls known as balotini. Alternatively, or in addition, the core may be of sufficiently openwork construction to allow sufficient light to penetrate to the underside of the tubing. To assist light penetration, reflecting means such as mirrors may be positioned adjacent the top of the core structure. Alternatively, sufficient illumination within the core may be provided by the inclusion of some form of artificial light source within the hollow centre of the core such as vertical fluorescent tubes. Such additional illumination may be employed continuously or only when necessary, for example at night or in very gloomy conditions. Such additional lighting may be set to give flickering illumination to maximise light useage.

Preferably the core structure is substantially cylindrical and the tube is wound helically on the cylinder. However, it will be appreciated that the core is not necessarily cylindrical and may, for example, be in the form of a truncated cone. Such a shape can be efficient for light utilisation in tropical countries where the sun shines vertically downwards, the conical structure minimising shadow formation. Preferably the method and apparatus are adapted for continuous production with means being provided for recycle of the synthesis mixture.

The synthesis mixture may be pumped to the top of the core structure and allowed to flow downwardly through the wound tube under turbulent conditions.

Alternatively, and preferably, the synthesis mixture may be pumped up the tube to a header tank, with suitable gases introduced at the base of the tube.

The method may be carried out under aerobic or anaerobic conditions. Thus carbon dioxide or air may be supplied to the tube or other gases such as oxygen or air/oxygen mixtures may be employed dependent on the synthesis product desired. Some plant synthesis reactions proceed anaerobically, in which case no such gaseous input is required.

In one preferred form of the invention, the fact that some biomass synthesis reactions proceed aerobically while some proceed anaerobically, can be utilised by providing two or more reactors as described above operating in series, a first reactor (or bank of reactors) being used to carry out an anaerobic reaction which leads to evolution of gas such as carbon dioxide, which, after separation of the first product biomass, is used in a second reactor for an aerobic reaction utilising the gas.

According to a further preferred form of the invention, ammonia gas is used as the, or as one of the nitrogen sources. The use of controlled ammonia injection has been found to be beneficial in minimising the growth of unwanted microscopic species, such as bacteria, amoeba and rotifers. It is believed that the presence of ammonium salts and ammonium ions inhibits such growth, while acting as a nutrient source for the growth of plant material such as Spirulina (blue green algae).

Alternatively, or in addition, such growth may be prevented by the use of selective ultraviolet irradiation of portions of the tube, such irradiation being applied internally or externally of the tube.

The nutrients for the synthesis may be provided at least in part by waste effluents such as those from sugar plants or petroleum refinery wastes or other high BOD carbohydrate wastes, the wastes thus being purified in the process, so that the biomass produced is a valuable biproduct of the effluent treatment process.

A particularly preferred tube material is polyethylene, especially low density polyethylene, which has excellent light transmission properties and low cost. It also has the valuable advantage of being resistant to attack by the biomass medium.

BRIEF DESCRIPTION OF THE DRAWINGS

The invention will now be described by way of example with reference to the accompanying drawings wherein.

DETAILED DESCRIPTION OF THE INVENTION

Figure 1:
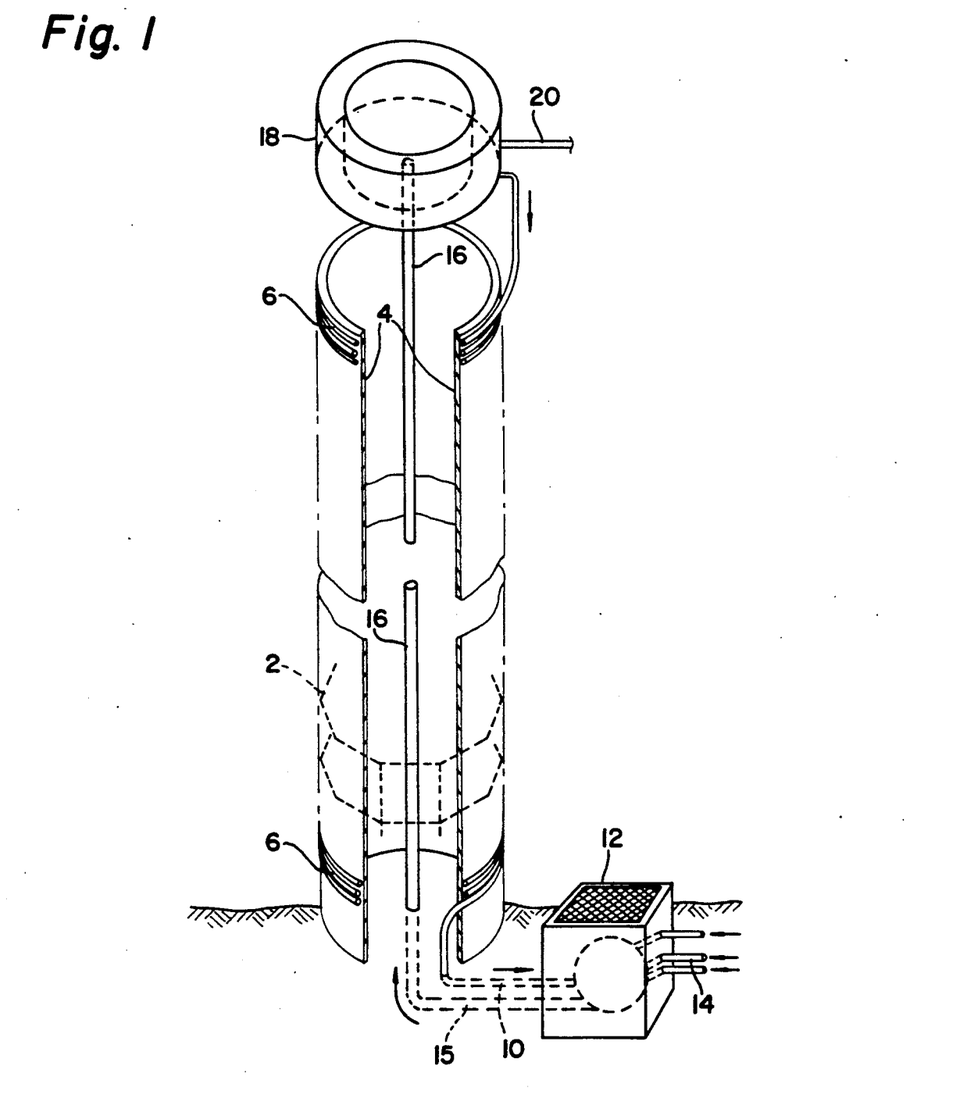
FIG. 1 is a diagrammatic view of a photobioreactor in accordance with the invention.

The photobioreactor shown in FIG. 1 comprises a core structure 2 (shown in dotted lines) which is upstanding and substantially cylindrical. The core structure may provide a continuous outer surface and be formed for example of hollow concrete sections. Dependent on the size of the reactor, the concrete sections may have internal access steps to enable inspection and maintenance personnel to enter the interior and reach apparatus positioned at the top part of the core structure. Alternatively, the core structure may be of openwork construction, for example it may be constructed of metal supports such as those known under the trademark "Dexion", or alternatively the core may be of cylindrical shaped metal mesh construction.

The support structure is faced with a layer 4 of a light reflective material such as aluminium foil. Over the light reflecting layer 4 is a spirally wound tube 6 of substantially transparent material. A preferred material is polyethylene, preferably of low density, as such tubing has excellent light transmission properties, low cost, and can be readily extruded and wound in long lengths. Polyethylene also has the advantage of good corrosion resistance and can withstand the chemical conditions of the reaction mixture to a much greater extent than a material such as stainless steel, which has conventionally been used in bulk fermentation methods. However other plastics materials such as methyl methacrylate or transparent polyvinyl chloride can be used, or even non plastics materials such as glass if capable of withstanding the conditions of use. The layer 4 of light reflective material may not be necessary in some circumstances if the tube 6 itself is half-silvered or otherwise treated so that it has a light reflecting surface adjacent the core structure 2. Pegs (not shown) may project from the core structure 2 to support the tube and prevent slippage of the windings.

If the core structure is of sufficiently open construction, the layer of light reflective material may not be needed as sufficient light will penetrate to the underside of the tubing. In order to allow sufficient light penetration to the interior of the core structure, the plastics tube windings should be spaced at least one quarter of the tube diameter apart. Suitably the tubing is wound at an angle to the horizontal of for example 3°.

If desired for reasons of strength, the tubing may have a reinforcing outer coating, for example of clear resin. This is especially valuable if it is desired to carry out the biomass production under considerable pressure.

The core structure may be solid, for example an existing tank which may be given a reflective surface and which optionally carries a mesh structure on which the tube windings are arranged. If desired, an outer mesh supporting structure may be additionally provided around the windings. The tanks may be of any desired diameter, e.g. from 2 to 5 meters.

The lower end of the core structure 2 is mounted in the ground and the lower end 10 of the tube 6 extends through the ground to a control pumping device generally indicated at 12. Pumping device 12, which can contain a diaphragm pump or any other suitable type of pump, is connected to supply lines 14 for, for example, carbon dioxide and/or air, nutrients and a nitrogen source, such as that provided by ammonia, ammonium salts, urea, compound fertilizers etc. The supply lines may conveniently be computer controlled. An outlet tube 15 carries the synthesis mixture from pumping device 12 up a central tube 16 arranged to extend up the hollow centre of core structure 2 to a header tank 18. Header tank 18 can contain any suitable launder means (not shown) to enable a product stream to be withdrawn on line 20. For example, more concentrated product rising towards the top of the mixture in the launder may be withdrawn by means of a weir device. Alternatively other separation means, such as a hydrocyclone, can replace the header tank 18. Line 20 is shown as extending from the side of header tank 18; however it may equally well extend down the centre of core structure 2 so that product is withdrawn at the base of the structure. The header tank also contains a purge system to remove excess air and recover the oxygen produced.

It will be appreciated that alternatively the synthesis mixture may be pumped up the coiled tube to the header tank 18, with suitable gases introduced at the base of the coiled tube, the return line 16 from the tank 18 to the pump having, if required, a flowmeter and/or a heat exchanger or like devices incorporated therein. Such a construction is described below with reference to FIG. 3.

The product stream on line 20 may pass to any suitable ancillary equipment for treating and/or extracting desired products from the biomass. It is particularly useful to pass the biomass through a solids/liquid or liquid/liquid contactor in cocurrent or countercurrent to a stream of a suitable immiscible extractant. A series of products may be extracted by contacting in a series of contactors with, if necessary, recycle of the raffinate phases between contactors. A suitable extractor is the bucket type contactor known as the Graesser contactor and described in GB patent specification No. 1,145,894 and U.S. patent specification No. 3,649,209.

The dimensions of the photobioreactor will vary dependent on the biomass production being carried out.

Figure 2:
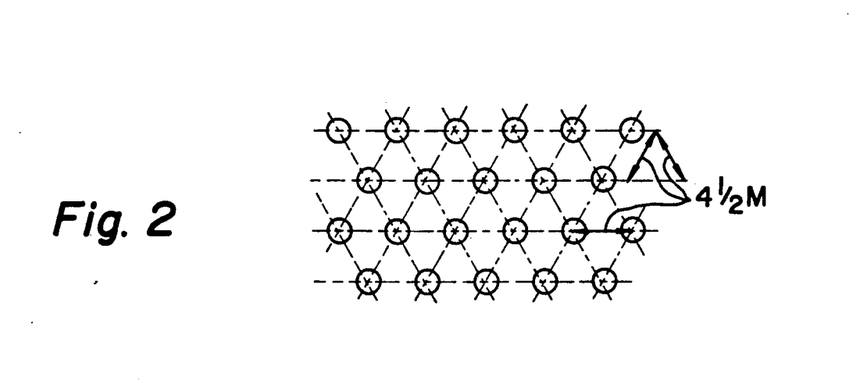
FIG. 2 is a sketch illustrating the layout of a plurality of such reactors.

One example is the production of biomass from Spirulina (blue green algae). In such a case the overall height of the core structure 2 may be, for example, 8 meters, with a core diameter of 2 meters. The wound tube 6 may then be of low density polyethylene of approximately 30 mm diameter, with the central tube 16 being of larger dimensions (approximately 120 mm) so as not to impede upward flow under control of the pump. It is calculated that such dimensions allow the core structure to carry approximately 1,347 meters of tubing giving a total surface area of 126 square meters, of which an area of about 100 square meters is effectively illuminated by the available natural light. The capacity of such a reactor is therefore approximately 1,269 liters. Because of the circular cross section of the reactor, a large number of such reactors can be positioned on a comparatively small area of ground as shown in FIG. 2. Thus by arranging the reactors in a close packing array, a minimum spacing of only 4 meters still allows maximum illumination of each reactor during daylight and minimises the effects of shadows.

While the above figures are given as an illustration of microbiomass production from Spirulina, it will be appreciated that a macrobiomass production can equally be carried out in a reactor having larger diameter tubing. An example is in carrying out photosynthesis of seaweed. However the diameter of the tubing should remain sufficiently small to encourage turbulence as the material passes downwards through the coil. Turbulence assists in preventing unwanted coating of the inside of the tube, thus increasing the working life of the plant. Preferably the turbulence is such as to give a Reynolds number of at least 2000, more preferably in excess of 3000. Furthermore high turbulence maximises the light usage in photosynthesis, as it allows the cells to receive intermittent exposure to light, thus allowing each cell to benefit from the essentially intermittent nature of photosynthesis.

It has been shown by previous workers that, by using flashing light rather than continuous light, the instantaneous growth rate is increased and the yield per unit of light energy raised in biomass production. Thus in a modification of the bioreactor shown in FIG. 1 a discontinuous curtain of highly polished thin and small aluminium shapes is arranged around the core structure 2 spaced therefrom and suspended from suitable means such as a rail at the top of structure 2. Even slight wind vibrates the shapes and results in light flashes over the tube area thus improving the growth rate. Alternatively or in addition, a similar curtain may be arranged within the hollow core. Alternative forms of curtains, such as metallic ribbons, may be employed to give a similar effect. A similar principle may be employed to improve growth rate if illumination, such as fluorescent tubing, is employed within the tube structure. The fluorescent tubes may thus be set to give flickering light action.

The photobioreactor shown has its pumping device 12 buried in the ground so as to maximise the space between each bioreactor, although of course the pumping device could be above ground level. In the example shown in FIG. 2 it will be seen that burying the pumping devices gives adequate spacing to allow the passage of servicing and product collection vehicles between the bioreactors. Such servicing may include provision for coping with extreme weather conditions, for example a heat exchanger included in the circuit and for example, in cold overnight conditions with the possibility of frost, it is possible to install removable insulated jackets positioned over the bioreactors when necessary. Likewise, in very hot conditions coolant can be sprayed on the reactors from external service devices. Alternatively, the bioreactors themselves may include provision for directing coolant spray onto the tubing 6 when desired, such as the provision of a water spray ring at the top of core structure 2 fed by a supply tube passing up the hollow core structure.

In a modification (not shown) of the reactor shown, the core structure 2 is mounted on a rotating platform with means provided for product withdrawal via a central circular launder leading to a tube extending to the base of the core structure. Such an arrangement has the advantage of using the rotational speed to influence flow characteristics in the tube and/or to influence the exposure time of the algae to sunlight.

Figure 3:
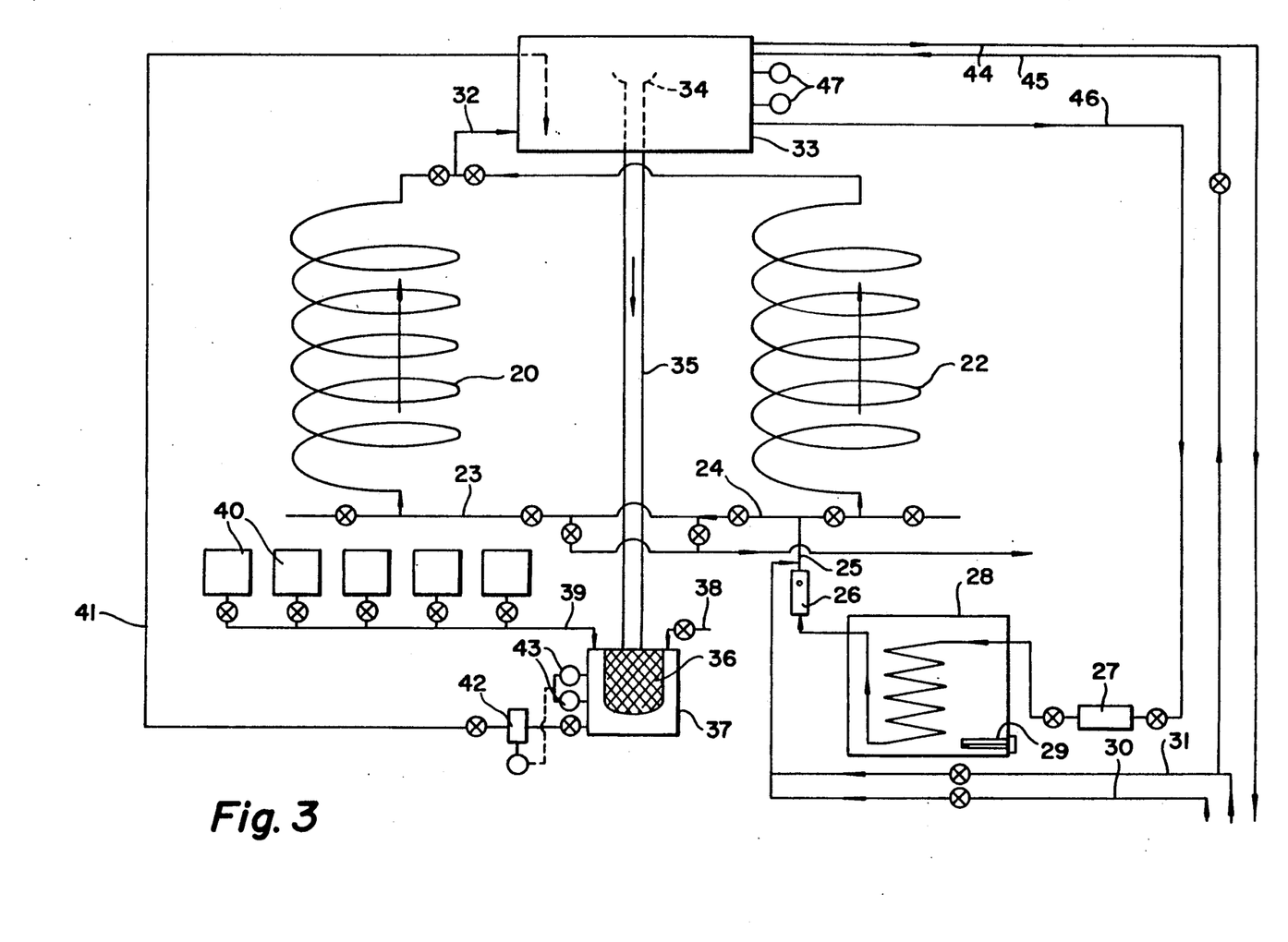
FIG. 3 is a flow diagram of an alternative method of biomass production.

An alternative method of biomass production suitable for use on a large scale uses the plant illustrated in FIG. 3. The plant comprises a pair of substantially transparent coiled tubes 20 and 22 arranged in parallel and each mounted on a suitable core structure (not shown). The coils may for example be of clear polyvinyl chloride tubing of 500 meters length and 30 mm diameter. A suitable core structure has been found to be a generally cylindrical white painted body, optionally also coated with reflective glass balls. It will be appreciated that, although two coils are shown, further coils may be employed. The synthesis mixture is fed to the coils 20 and 22 via lines 23 and 24 from a single line 25 which is supplied via flowmeter 26 with recirculating reactants pumped by pump device 27 (suitably a diaphragm pump). Before reaching line 25, the recirculating reactants pass through heat exchange unit 28 provided with immersion heater 29. Unit 28 serves to provide heat if necessary in cold weather, or alternatively to remove heat during hot ambient conditions. Carbon dioxide and air are also supplied to line 25 via suitable flowmeters (not shown) on lines 30 and 31 respectively.

At the top of the coils 20 and 22, the flowing synthesis mixtures join in line 32 for passage to header tank 33 with an overflow harvester device 34 which allows mixture to flow downwardly through return pipe 35 to a bag filter 36 in which product biomass (e.g. algae) is collected and periodically withdrawn. The bag is of a mesh which retains large mature algae while allowing smaller growing algae to pass through. Bag filter 36 is disposed in filter unit 37 supplied with make-up water on line 38 and nutrients on line 39 from a series of nutrient supply vessels 40. Filtrate in unit 37 with added water and nutrients is returned on line 41 to header tank 33 under the action of pump 42 which is responsive to level control valves 43.

Excess carbon dioxide (and/or other gaseous products) are withdrawn from header tank 33 on line 44. When necessary air is supplied to header tank 33 on air purge line 45. Circulating synthesis mixture not passing down overflow 34 returns to pump 27 on line 46.

Circulation in the system and harvesting of product are controlled by electronically operated pressure control values 47, which are brought into operation after start up once optimum synthesis conditions have been achieved (as determined for example by optical density measurement).

It will be noted that in the apparatus described above, the synthesis mixture is pumped up the coils and product flows downwardly under gravity through return pipe 35. Such an arrangement has the advantage that the carbon dioxide supply has a relatively long time to contact the growing algae for conversion before release into header tank 33. (If excess carbon dioxide remains in exit line 44, then the feed of carbon dioxide is reduced). Furthermore the straight and comparatively long down return pipe 35 to the filter bag 36 gives a high velocity which prevents clogging.

It will be appreciated that the bioreactors shown in the above Figures are easy to assemble and if wished can be constructed in modular form. Thus the tubular coil can readily be constructed in sections with valves and junctions allowing reaction products to be removed as needed and/or any necessary additional nutrient feed introduced. This is expecially useful for rapid reactions, such as certain fermentation reactions.

Although pump operation has been described above for providing the motive force necessary to give highly turbulent flow in the tubing, as is often desirable, in some reactions it is desirable to employ lower flow conditions, for example, where the product cells are of a delicate nature. In such cases it may be sufficient to employ air and/or other gaseous supply as the lift to sustain circulation. If need be a compressed gas venturi jet or a steam jet may be employed. Steam injection is particularly suitable where a certain amount of heat is required for growth.

Figure 4:
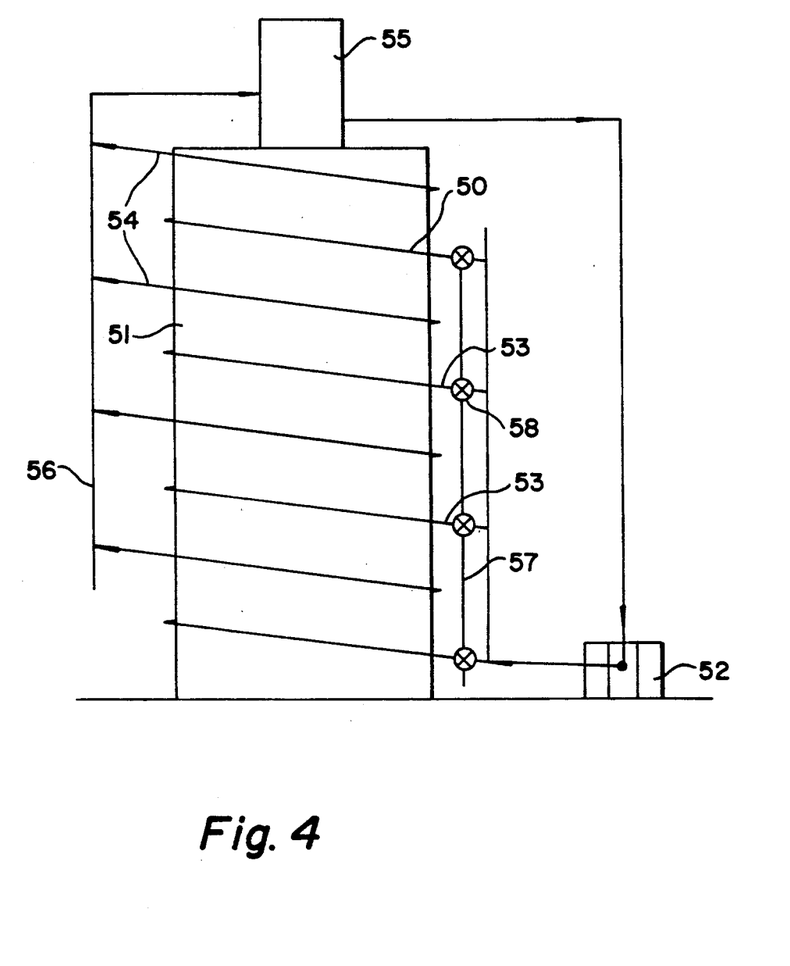
FIG. 4 is sketch of a modified bioreactor.

When using tubular modules, provision may be made for intermediate pumps, and/or air or steam injection so as to control the flow rates through the tubing even for long flow passages. This is particularly valuable when the reaction medium has a tendency to become viscous, for example in certain fermentation processes. FIG. 4 schematically illustrates a modified reactor which embodies provisions to overcome problems of pressure drop (and also possible elongation of the tubing when warm, e.g. at 35° C.). Thus a coil 50 is arranged in sections on core 51. Synthesis mixture is pumped up the coil via the recycle pump and heat exchanger unit 52 but, instead of being all introduced at the bottom of the coil, it is introduced therealong on a series on inlet lines 53. Air and $CO_2$ are also introduced to each line 53 via a feed main 57 having valve entries 58 to each line 53. Similarly outlet lines 54 lead from each coil section to header tank 55 via rising main 56. It is advantageous to construct rising main 56 so that it can move on the side of the coil to cater for expansion of the tubing. Thus the main may be flexible or may be rigid but provided with a flexible mounting. The lengths of tube in each coil section will vary according to flow rate, tubing bore and tower height etc. but approximately eight sub units with lengths of about 300 meters and 20 mm tubing bore have been found to be suitable.

The method and apparatus described above are applicable to a wide range of biomass production processes. If desired, the feed system to the reactor can be controlled to introduce small amounts of one or more trace elements such as selenium, cobalt, copper, zinc, gallium and germanium under varying conditions to alter trace element amounts. It will be seen that the process allows the production of single strain pure biomass from, for example, algae and seaweed under controlled conditions to give a pure and consistent product. Dependent on the ancillary processing employed, the concentration of certain valuable products in the biomass can be increased. It has been found that algae and other simple organisms can form solubilised complexes, usually proteins, which are beneficial or even essential to human and animal well being. For example, a high concentration of lipid containing gamma linolenic acid (GLA) can be obtained from Spirulina. Alternatively high grade agar may be produced from Gracilaria or beta-carotene from Dunaliella. If the process being carried out results in an increase in colour density in the reactor (due to increased quantities of water soluble natural pigments), pigment removal means (such as chromatographic separation, or solvent extraction, possibly employing a Graesser contactor as described above) may be incorporated, suitably associated with pigment recovery means. The build-up of excessive pigmentation which adversely affects light penetration is thus preserved. Such pigments include chlorophylls, carotenes, phycocyanins and phycoerythins.

It will be appreciated that considerable variation is possible in the nutrients supplied to the bioreactor and the operating conditions.

It has been found of value to use ammonia gas as one of the nitrogen sources, or as the sole nitrogen source. Controlled injection of ammonia gas, while promoting the growth of an organism such as Spirulina, inhibits the growth of unwanted microscopic life such as bacteria, amoeba and rotifers. This is of considerable commercial importance as the growth of such microscopic species has been a major problem in previously proposed methods for biomass production. Other gases which inhibit bacterial growth, such as carbon monoxide, may be employed.

As an alternative, or in addition, bacterial invasion problems may be at least partially alleviated by the use of ultraviolet irradiation of sections of the tubing. This may, for example, be accomplished by winding an ultraviolet emitting coil around one or more portions of the tubings and/or by the inclusion of an ultraviolet emitting tube withing the tubing itself, suitably in a specially widened tubing section.

The reactor described above is suitable for use for both aerobic and anaerobic biomass production processes. Thus gases such as carbon dioxide or air may be used, for example for Spirulina and Chlorella production, while air/oxygen mixtures or oxygen alone may be employed for certain processes such as yeast growth. Anaerobic processes may be carried out, such as the cultivation of *Rhodopseudomonas Palustris* using as nutrient high BOD (biological oxygen demand) carbohydrate waste, a reaction which produces carbon dioxide. Alternative processes include the growth of Norcadia, Candida and other Pseudomonas organisms for degradation of hydrocarbons to carbon dioxide.

According to a useful further embodiment of the invention, two bioreactors, or banks of bioreactors, may be joined in series, the first being used for an anaerobic reaction, such as the growth of *Rhodopseudomonas Palustris* or *Acidophila* which produces $CO_2$, while the second reactor utilises the $CO_2$ in the cultivation of $CO_2$—utilising, oxygen-producing algae such as Chlorella or Spirulina. Such a system is illustrated in FIG. 5.

Figure 5:
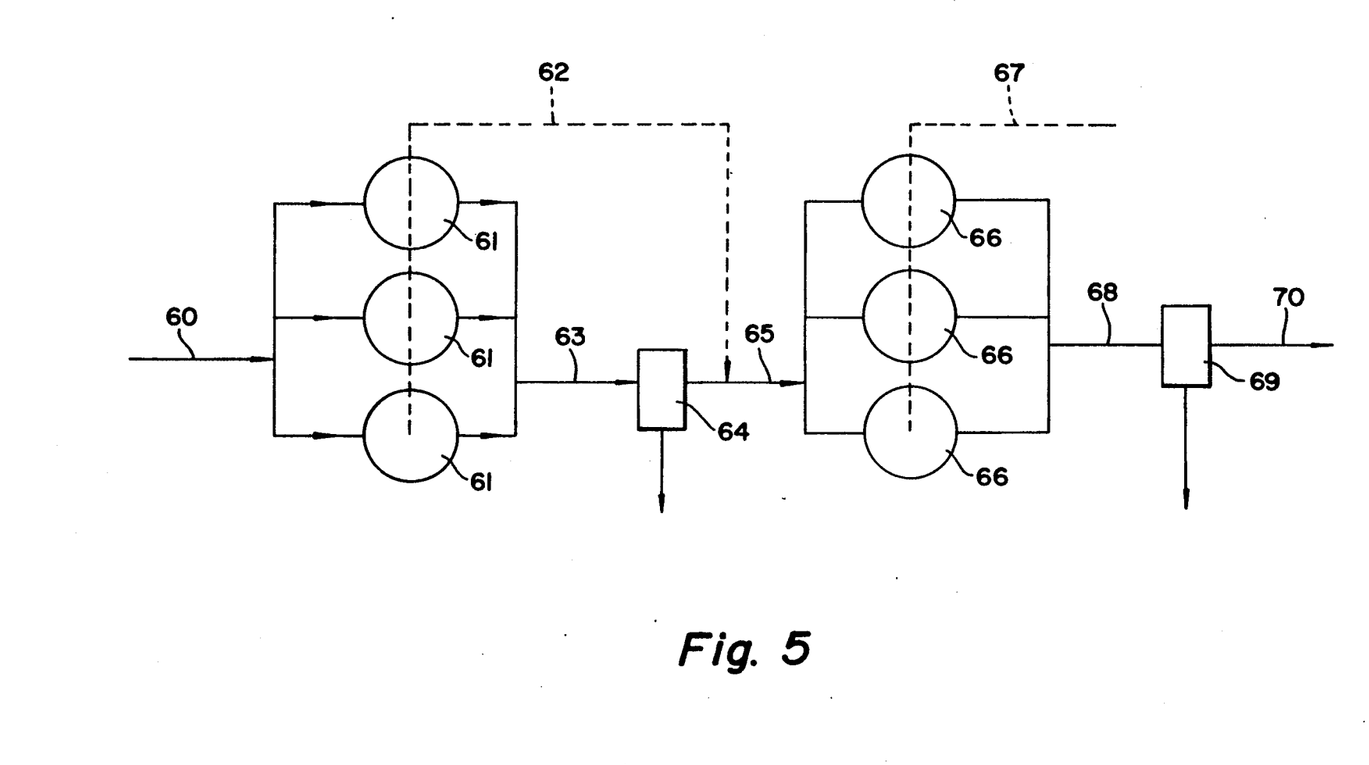
FIG. 5 is a flow diagram of two banks of photobioreactors operating in series.

In the flow diagram of FIG. 5, a high BOD effluent liquor is passed on line 60 to a first bank of reactors 61 as nutrient for the cultivation of a carbon dioxide-producing organism such as *Rhodopseudom acidophila*. Carbon dioxide produced in reactors 61 is withdrawn on line 62. Liquor from reactors 61 is withdrawn on line 63 to filter unit 64, where solid biomass is withdrawn. The carbon dioxide stream in line 62 is combined with the liquor from filter 64 in line 65 for passage as nutrient to a second bank of reactors 66 for the cultivation of a carbon dioxide-consuming, oxygen-producing organism such as Spirulina. Oxygen is withdrawn on line 67 for any suitable purpose, while the liquor withdrawn on line 68 is filtered in unit 69 to give a solid biomass product. The remaining effluent on line 70 has a considerably reduced BOD value.

Of course further stages may be added and any desired number of reactors may be used in each bank. Any other gases produced in the first reactors may be used in subsequent bioreactors or for other purposes. The use of a plurality of reactors can also prove useful when the first reactor is used for example for the growth of a water splitting algae such as *Chalydamonas Reinhardtii* which produces hydrogen and oxygen as gaseous products, which are separated and the oxygen used in the second reactor for an oxygen consuming substance.

The provision of a continuously operable process with recycling of the mixture keeps the consumption of gases and nutrients as low as possible with minimum wastage. Product oxygen can be used in any adjacent chemical plant. Any heat produced can be employed in heat exchange. High biomass densities can be obtained, of up to 7, or even 40, times the densities obtainable in open channel photosynthesis processes. Even derelict and uneven land can be utilised and the size of the installation can readily be expanded to fill growing needs. The use of angled units maxmimises light usage and even diffuse light can be effectively utilised. Thus the possible latitude ranges for biomass production are comparatively wide and even the light of an overcast English winter day is found to be sufficient for algae or seaweed growth. Only low grade heat at most is required even in a severe winter to keep a temperature minimum of approximately 10° C. In severe weather, it has been found advantageous to insulate the tubing with an outer curtain of transparent polyethylene sheeting. Cooling in summer is desirable to maintain a maximum temperature of approximately 35° C. The use of turbulent conditions enables long running periods before the need for cleaning, so that shut down periods are kept to a minimum. In any case cleaning of the tubing is a comparatively straightforward operation and can be effected by forcing a cleaning "bullet" through the tubing. This in contrast to the problems encountered in cleaning conventional fermentation tanks where contamination often has to be scraped from the walls.

It will be seen that the system described above lends itself to automatic control and the whole arrangement of modules can be computer controlled, thereby saving labour. A further advantage is that part of such a multi-module system can be switched, if required, from producing one type of product to another, without the need for major plant modifications.

We claim:

1. An apparatus comprising:
    an upstanding substantially cylindrical support structure;
    a substantially transparent tube supported by the support structure and wound helically on the outside thereof so that, in use, the exterior of the wound tube is exposed to natural light, said tube containing at least living plant matter;
    a header tank at the top of the support structure, the upper end of the transparent tube being connected to the header tank;
    a pipe extending from the header tank to the bottom of the support structure, said pipe being connected to the lower end of the transparent tube;
    means for causing a synthesis mixture to flow under turbulent conditions through the tube, the header tank and the pipe; and
    means for withdrawing a biomass synthesis product from at least one of the header tank and the wound tube.

2. An apparatus as claimed in claim 1, in which the support structure is hollow and comprises a wall of cylindrical form and which is of open mesh construction providing openings to permit light to pass through the openings in the wall.

3. An apparatus as claimed in claim 2, in which the tube is wound at an angle to the horizontal of about 3°, and adjacent turns of the tube are separated by a distance equal to at least one-quarter of the diameter of the tube.

4. An apparatus as claimed in claim 1, further including light reflecting means located between the tube and the outside of the support structure.

5. An apparatus as claimed in claim 1, wherein the cross-sectional area of the pipe is greater than that of the helically wound tube.

6. An apparatus as claimed in claim 1, wherein the cross-sectional area of the pipe is greater than that of the helically wound tube.

7. An apparatus as claimed in claim 1, in which the tube is wound in a plurality of sections one above the other on the support structure, each section having an inlet end and an outlet end, said inlet ends being connected together and said outlet ends being connected together and the synthesis mixture is caused to flow through said sections of tube in parallel.

8. An apparatus comprising:
    an upstanding substantially cylindrical support structure;
    a header tank at the top of the support structure;
    a substantially transparent tube supported by the support structure and wound helically on the outside thereof so that, in use, the exterior of the wound tube is exposed to natural light, said tube being arranged in a plurality of separate sections, each having an inlet end and an outlet end and arranged one above the other on the support structure, and said tube containing at least living plant matter;

a pump having an inlet port and an outlet port;

the inlet ends of the sections of the tube being connected together and to the outlet port of the pump, the outlet ends of the sections of the tube being connected together and to the header tank;

a pipe extending from the header to the inlet port of the pump, the pump being operated to cause a synthesis mixture to flow through the sections of wound tube in parallel under turbulent conditions; and means for withdrawing a biomass synthesis product from the header tank.

* * * * *